(12) United States Patent
Delaney et al.

(10) Patent No.: US 11,634,859 B2
(45) Date of Patent: Apr. 25, 2023

(54) METHODS OF TREATING FABRICS WITH ORGANIC ACIDS AND RELATED TREATMENT COMPOSITIONS

(71) Applicant: The Procter & Gamble Company, Cincinnati, OH (US)

(72) Inventors: Sarah Ann Delaney, Hebron, KY (US); Genevieve Cagalawan Wenning, Villa Hills, KY (US); Sol Melissa Escobar, Mason, OH (US); Bryan Douglas Dickerson, Independence, KY (US)

(73) Assignee: The Procter & Gamble Company, Cincinnati, OH (US)

( * ) Notice: Subject to any disclaimer, the term of this patent is extended or adjusted under 35 U.S.C. 154(b) by 217 days.

(21) Appl. No.: 17/173,618

(22) Filed: Feb. 11, 2021

(65) Prior Publication Data
US 2021/0254274 A1 Aug. 19, 2021

Related U.S. Application Data

(60) Provisional application No. 62/975,876, filed on Feb. 13, 2020.

(51) Int. Cl.
*D06M 13/00* (2006.01)
*D06M 13/192* (2006.01)
*G01N 33/36* (2006.01)

(52) U.S. Cl.
CPC ........ *D06M 13/192* (2013.01); *G01N 33/367* (2013.01)

(58) Field of Classification Search
CPC . D06M 13/192; G01N 33/367; C11D 3/2086; C11D 7/265; C11D 11/0017; C11D 3/2075
USPC .......................................................... 8/137.5
See application file for complete search history.

(56) References Cited

U.S. PATENT DOCUMENTS

| | | |
|---|---|---|
| 2004/0220072 A1 | 11/2004 | Trinh et al. |
| 2013/0111675 A1 * | 5/2013 | Soontravanich ..... C11D 3/0036 252/193 |
| 2016/0186096 A1 | 6/2016 | Eberhardt et al. |
| 2018/0051236 A1 * | 2/2018 | Soontravanich .... C11D 11/0023 |
| 2018/0195024 A1 | 7/2018 | Piorkowski |
| 2019/0298630 A1 | 10/2019 | Dixon et al. |
| 2020/0080028 A1 | 3/2020 | Fuentes Ferrando et al. |
| 2020/0140789 A1 * | 5/2020 | Delaney ................. C11D 3/50 |

(Continued)

FOREIGN PATENT DOCUMENTS

| | | | | |
|---|---|---|---|---|
| EP | 3650524 A1 * | 5/2019 | ............... | C11D 3/20 |
| WO | 2010025097 A1 | 3/2010 | | |

OTHER PUBLICATIONS

15723 PCT Search Report and Written Opinion for PCT/US2021/017572 dated May 3, 2021, 15 pages.

*Primary Examiner* — Eisa B Elhilo
(74) *Attorney, Agent, or Firm* — Andrew J. Mueller (57) ABSTRACT

Processes and uses related to treating fabrics with an organic acid, such as citric acid with certain treatment liquors or consumer product treatment compositions. A process to determine the presence of a metal-based residue on a fabric. Uses of a treatment composition or a treatment liquor to rejuvenate a non-white color of a fabric. Processes to demonstrate and/or display the color-rejuvenation benefits of a treatment composition.

17 Claims, 4 Drawing Sheets
(3 of 4 Drawing Sheet(s) Filed in Color)

(56) References Cited

U.S. PATENT DOCUMENTS

2020/0140791 A1* 5/2020 Delaney ............... C11D 3/2044
2020/0157476 A1* 5/2020 Applegate ............ C11D 3/2079

* cited by examiner

Fig. 7

METHODS OF TREATING FABRICS WITH ORGANIC ACIDS AND RELATED TREATMENT COMPOSITIONS

FIELD OF THE INVENTION

The present disclosure relates to various processes and uses related to treating fabrics with an organic acid, such as citric acid, with certain treatment liquors or consumer product treatment compositions. The disclosure relates to a process to determine the presence of a metal-based residue on a fabric. The disclosure relates to the use of a treatment composition to rejuvenate a non-white color of a fabric. The disclosure relates to processes to demonstrate the color-rejuvenation benefits of a treatment composition.

BACKGROUND OF THE INVENTION

When a fabric, such as a garment, is treated with a water that contains metal ions, such as ions due to water hardness or from treatment additives such as detergents, certain metal-related residues may remain on the fabric. These residues may be particularly prevalent when the fabrics are washed with detergents in hard water, as the metal ions (e.g., calcium and/or magnesium ions) in the water may react with salts (such as carbonates) or surfactants (such as linear alkyl benzene sulphonates) to form insoluble precipitates that deposit on the fabrics. Metal-based residues may even build up in the absence of treatment with detergent, such as when bath towels or shower curtains are exposed to hard water. These residues may build up over time due to repeated uses or wash cycles.

Some consumers may be particularly sensitive to such residues and may want them removed from the fabrics as efficiently as possible. Additionally or alternatively, the consumers may want to be able to easily test their fabrics for the presence of such residues.

Furthermore, these residues can negatively impact the color of the fabric, for example by making the fabric appear faded. Consumers may (erroneously) believe that the dyes of the fabrics have faded, and that a return to a more vibrant color is impossible, or may require interventions that make use of synthetic ingredients, such as synthetic polymers. Thus, the consumer may discard a faded garment, contributing to landfill waste. There is a need for environmentally friendly ways to restore the color of a fabric and/or to extend its useful life. Additionally, such residues are not readily visible to the naked eye. Manufacturers of consumer products that remove such residues desire effective ways of demonstrating the efficacy of, and/or the perceived need for, their products.

There is a need for products, uses, and/or processes that meet one or more of these needs.

SUMMARY OF THE INVENTION

The present disclosure relates to various products and uses. For example, the present disclosure relates to a process to determine the presence of a metal-based residue on a fabric. The present disclosure also relates to a use of a treatment composition to rejuvenate a non-white color of a fabric, for example where the fabric has been previously washed with a laundry detergent. The present disclosure also relates to a use of a treatment liquor to rejuvenate a non-white color of a fabric, for example where the fabric includes a metal-based residue. The present disclosure also relates to processes to demonstrate or display the color-rejuvenation benefits of a treatment composition.

BRIEF DESCRIPTION OF THE DRAWINGS

The patent or application file contains at least one drawing/photograph executed in color. Copies of this patent or patent application publication with color drawings/photographs will be provided by the Office upon request and payment of the necessary fee.

The figures herein are illustrative in nature and are not intended to be limiting.

DETAILED DESCRIPTION OF THE INVENTION

The present disclosure relates to various processes and uses related to treating fabrics with organic acids, or treatment compositions that contain such organic acids. The organic acids or compositions that contain them can be useful for detecting or removing certain residues, and/or for rejuvenating fabric colors when such residues have been deposited on the fabric. The processes and uses described herein provide useful methods for detecting, illustrating, or comparing such benefits. The processes, uses, and treatment compositions are described in more detail below.

As used herein, the articles "a" and "an" when used in a claim, are understood to mean one or more of what is claimed or described. As used herein, the terms "include," "includes," and "including" are meant to be non-limiting. The compositions of the present disclosure can comprise, consist essentially of, or consist of, the components of the present disclosure.

The terms "substantially free of" or "substantially free from" may be used herein. This means that the indicated material is at the very minimum not deliberately added to the composition to form part of it, or, preferably, is not present at analytically detectable levels. It is meant to include compositions whereby the indicated material is present only as an impurity in one of the other materials deliberately included. The indicated material may be present, if at all, at a level of less than 1%, or less than 0.1%, or less than 0.01%, or even 0%, by weight of the composition.

As used herein the phrase "fabric care composition" includes compositions and formulations designed for treating fabric. Such compositions include but are not limited to, laundry cleaning compositions and detergents, fabric softening compositions, fabric enhancing compositions, fabric freshening compositions, laundry prewash, laundry pretreat, laundry additives, spray products, dry cleaning agent or composition, laundry rinse additive, wash additive, post-rinse fabric treatment, ironing aid, unit dose formulation, delayed delivery formulation, detergent contained on or in a porous substrate or nonwoven sheet, and other suitable forms that may be apparent to one skilled in the art in view of the teachings herein. Such compositions may be used as a pre-laundering treatment, a post-laundering treatment, or may be added during the rinse or wash cycle of the laundering operation.

Unless otherwise noted, all component or composition levels are in reference to the active portion of that component or composition, and are exclusive of impurities, for example, residual solvents or by-products, which may be present in commercially available sources of such components or compositions.

All temperatures herein are in degrees Celsius (° C.) unless otherwise indicated. Unless otherwise specified, all measurements herein are conducted at 20° C. and under the atmospheric pressure.

In all embodiments of the present disclosure, all percentages are by weight of the total composition, unless specifically stated otherwise. All ratios are weight ratios, unless specifically stated otherwise.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Processes and Uses

The present disclosure relates to various processes and uses related to treating fabrics. The processes and uses may further relate to determining the presence of certain residues, demonstrating the removal of such residues, and/or rejuvenating the color(s) of a fabric. The processes may employ a treatment composition, which is described in more detail below.

Demonstrating Residue Removal

The present disclosure relates a process to determine the presence of a metal-based residue on a fabric, such as a garment. Such processes may be useful to consumers who wish to test their own garments for residues. Such processes may also be useful to manufacturers or advertisers who wish to demonstrate the need for or efficacy of their treatment compositions, for example by showing consumers visual evidence of otherwise-unseen residues on their clothes. Because these residues are not readily visible to the naked eye, it is useful to provide a real-time visualization regarding (and removal) of the residues. The processes can be used to determine the presences of a metal-based residue on a fabric; the process can also (alternatively or additionally) be used to demonstrate the removal of a metal-based residue on a fabric.

The process to determine the presence of, and/or to demonstrate the removal of, a metal-based residue on a fabric may include the step of providing a vessel with a storage portion and an open mouth. The vessel may include a base wall and one or more side walls. The storage portion is formed by the base wall and one or more side walls (for example, a front wall, a back wall, a right-side wall, and a left-side wall). The one or more side walls may be relatively flat, curved, or a combination thereof.

The base wall, the one or more side walls, or a combination thereof may include a transparent portion. The base wall, the one or more side walls, or a combination thereof may be made of a transparent material, such as glass (including borosilicate glass) or plastic. Transparent portions and/or transparent material is useful so that the residue presence/removal can be visually seen through the walls.

The open mouth is in communication with the storage portion of the vessel, optionally via a neck. The open mouth may be opposite the base wall. A relatively wide mouth (e.g., at least 5 cm, preferably at least 10 cm in width) may be preferred, so that materials such as water, a treatment composition, a treatment liquor, and/or a fabric sample can be conveniently added to the storage portion.

Suitable vessels may include pans, drinkware, aquariums, jars, or beakers. Materials placed into the vessel may be viewed from above, for example via the open mouth, from the side of the vessel via a transparent portion of a side wall, or from the bottom of the vessel via a transparent portion of the base wall. The vessel may be characterized by an internal volume of from about 500 mL to 5 L, preferably from about 1 L to about 2 L.

Figure 1:
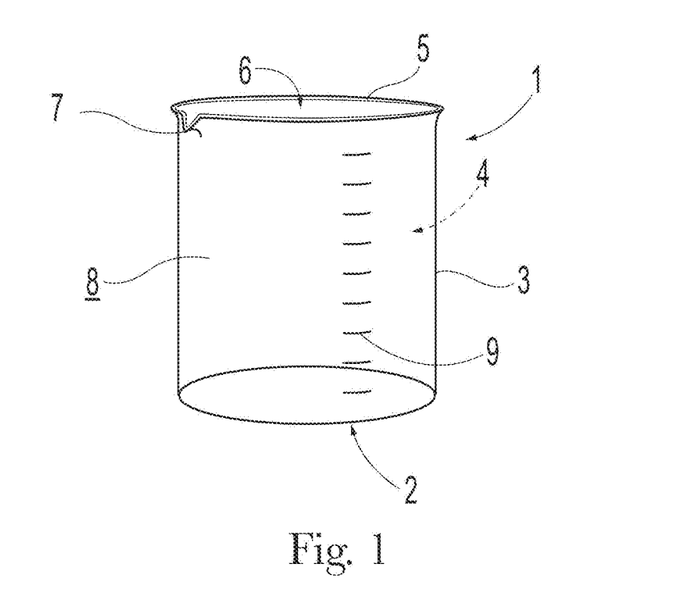
FIG. 1 shows a perspective view of an exemplary vessel, namely a beaker.

FIG. 1 shows a depiction of an exemplary vessel 1, namely a beaker. The vessel 1 comprises a base wall 2 and a cylindrically shaped side wall 3. The base wall 2 and the side wall 3 cooperate to form a storage volume 4. The side wall 3 terminates in a rim 5 at an end of the side wall 3 located away from the base wall 2. The rim 5 defines an open mouth 6 of the vessel 1. The vessel 1 includes a spout 7. The material 8 of the beaker is generally transparent, although the walls may comprise indicia 9 such as brand names, volume labels, and/or graduation markings.

The storage portion of the vessel may comprise a treatment liquor. The treatment liquor may be an aqueous liquid. The treatment liquor comprises an organic acid, as described in more detail below. The treatment liquor may be characterized by an acidic pH, preferably a pH of from about 1 to about 6, or from about 2 to about 5, or from about 3 to about 5, or from about 3 to about 4. Acidic pHs may be preferred to improve residue removal.

The treatment liquor may be substantially transparent prior to the addition of the fabric. For example, the treatment liquor may be characterized by a percent transmission (% T) of at least 90%, or at least 95%, or at least 98%. A substantially transparent treatment liquor may be preferred to facilitate easier detection, viewing, or analysis of the removed residues.

The process may comprise the step of providing a treatment liquor to the storage portion of the vessel. The treatment liquor may be formed by combining a treatment composition with water; the treatment composition may provide the organic acid, preferably citric acid. Suitable treatment compositions are described in more detail below. The treatment composition may be a liquid rinse-added composition and may have less than 5 wt %, or less than 3 wt %, or less than 1 wt %, or be substantially free of surfactant, such as anionic surfactant. The treatment composition may be a liquid detergent, for example an acidic liquid detergent.

Water may first be provided to the storage portion, followed by a step of providing the treatment composition to the storage portion (and the water already found therein); this order of steps may be preferred for safety reasons—the treatment composition may be characterized by an acidic pH, and typically one should do as one ought to and add acid to water. Alternatively, the treatment composition may be first provided to the storage portion, followed by the addition of water. As another alternative, the water and treatment composition may be combined in a separate container and then added to the vessel. As yet another alternative, the treatment liquor may be simply the treatment composition, which may be an aqueous composition, provided neat to the vessel (e.g., in the absence of additional water).

The process may further comprise the step of providing a fabric. The fabric may be a prewashed fabric. The prewashed fabric may have been previously treated with a laundry detergent in one or more wash cycles, preferably at least two, or at least three, or at least 5, or at least 8, or at least 10 wash cycles. The more times a fabric has been treated by a laundry detergent, the more residue is likely to be deposited on the fabric, thereby being easier to show the presence and/or removal of the residue. The laundry detergent may be a liquid detergent, a powdered detergent, or a mixture thereof, preferably a powdered detergent. Powdered detergents may be preferred as they may provide relatively more residues than liquid detergents, such as carbonate or silicate salts.

The fabric, preferably the prewashed fabric, may have been treated with water comprising metal ions. The metal ions may result in residue, for example by interacting with components of laundry detergent and forming metal-based residues that deposit on the fabric. The metal ions may be selected from calcium ions, magnesium ions, copper ions, aluminum ions, or mixtures thereof, preferably calcium ions, magnesium ions, or mixtures thereof, more preferably calcium ions. The water used to treat the prewashed fabric may be characterized by a hardness of from about 0 to about 30 grains per gallon (gpg), or from about 1 to about 30 gpg, or from about 2 to about 30 grains per gallon, or from about 5 to about 20 gpg, or from about 5 to about 15 gpg, or from about 5 to about 10 gpg. The water may include from about 15 to about 200 ppm calcium, or from about 20 to about 175 ppm calcium, or from about 50 to about 100 ppm calcium. The water may include calcium and magnesium ions present in a weight ratio of from about 2:1 to about 5:1, or from about 3:1 to about 4:1.

The fabric may have a color. The color may be a non-white color, which may also exclude near-white colors such as off-white, ivory, cream, beige, and the like. The color may be a relatively dark color. It may be preferred to use a fabric having a non-white color and/or a relatively dark color in order to provide better contrast with the residues that may be removed from fabric during the presently described process. The color may be black, gray, or blue, preferably black to provide the greatest degree of contrast.

The fabric may comprise a metal-based residue located on the fabric. The metal of the metal-based residue may be selected from the group consisting of calcium, magnesium, copper, aluminum, or mixtures thereof, preferably calcium, magnesium, or mixtures thereof, more preferably calcium. The metal-based residue may be characterized by a solubility of less than Ig per 1000 g deionized water, measured at 22° C., preferably less than 0.5 g per 1000 g deionized water, or even less than 0.1 g per 1000 g deionized water. Lower solubilities indicate a greater likelihood to precipitate and deposit onto a fabric during a treatment cycle.

The metal-based residue may be derived from an anionic surfactant, an anionic polymer, a carbonate, a silicate, or a combination thereof. The anionic surfactant may comprise a sulphonated surfactant, a sulfated surfactant, a carboxylated surfactant, or a mixture thereof, preferably an alkyl benzene sulfonate, an alkyl sulfate, an alkyl alkoxylated sulfate, or mixtures thereof. The anionic polymer may comprise carboxymethyl cellulose, a polycarboxylate polymer, or a mixture thereof. The anionic surfactant, anionic polymer, carbonate, and/or silicate may have been provided by the detergent used to prewash the fabric. Without wishing to be bound by theory, metal ions present in a wash liquor may interact with ionized forms of one or more of these components (or others) to form an insoluble precipitate that may deposit onto a fabric.

The process may comprise the step of submerging a portion of the fabric in the treatment liquor. The "portion" may include a part or the whole of the fabric. The portion of the fabric may be submerged for a minimum period of time to allow the treatment liquor to interact with the fabric, and to remove at least some of the metal-based residue, if any. The portion of fabric may be submerged for at least two seconds, or at least three seconds, or at least five seconds, or at least ten seconds, or at least 15 seconds, or at least 30 seconds, or at least 60 seconds, or at least 120 seconds, or at least 180 seconds. Longer periods of time are more likely to lead to greater degrees of residue indication and/or removal. The submerged portion of the fabric may be pulled taut, for example with the use of a frame or support, to provide maximum surface area for treatment and/or a flat surface against which the removed residues may conveniently be seen. The fabric may be nearly as wide as the storage volume and/or the open mouth, and/or nearly as tall or even taller, so as to provide a large surface areas upon which the treatment liquor can act, thereby tending to produce a relatively larger amount of removed residue in the treatment volume.

After the fabric is or has been submerged, the process may include the step of detecting the presence of released residue in the treatment liquor. The released residue may take the form of a solid, a gas, or a combination thereof. The detection step may include determining the presence of solids and/or gasses in the treatment liquor. The process may include performing a visual inspection and/or a spectrophotometric test to determine whether solids are present in the treatment liquor.

The detection step may take place while the fabric is still submerged. The fabric may be removed from the treatment composition during or prior to the detection step. A portion of the treatment composition may be removed from the vessel for the detection step, e.g. for analysis of the presence of a solid and/or gas.

The presence of a solid or gas in the treatment liquor may manifest in the form of turbidity, cloudiness, haziness, or looking like wisps of smoke. The presence of a solid, gas, and/or an increase in turbidity may be associated with the removal of metal-based residues from the fabric, indicating that such residues were indeed located on the fabric and/or are being removed/dissolved.

The detection step may comprise a visual inspection. For example, an observer may view the resulting treatment liquor through a transparent portion or the open mouth of the vessel and look for solids or off-gassing, for example in the form haziness, cloudiness, or "wisps of smoke." The detection step may comprise determining the relative transparency of the resulting treatment liquor, for example by determining the percent transmittance (% T) with a spectrophotometer; lower % T values (e.g., less than 100%) compared to a blank of treatment liquor prior to contacting the fabric may indicate the presence of removed residue. The resulting treatment liquor may be characterized by a % T of less than 80%, or less than 70%, or less than 60%, or less than 50%.

Turbidity may be assessed using the Turbidity Method provided in the Test Methods section below.

The process may further comprise displaying the results of the process, such as with a photograph or a video. The solid or gas may be shown or displayed as being visible in the treatment liquor (e.g. evidenced by cloudiness). Solid residues may be collected, for example by centrifuging or filtering, and displayed. The fabric may be analyzed for residue removal, for example by weighing before and after the treatment.

Use for Color Rejuvenation

The present disclosure also relates to the use of a particular treatment composition to rejuvenate a non-white color of a fabric. The fabric may comprise a metal-based residue. The fabric may have been previously washed with a laundry detergent. As mentioned above, metal-based residues derived from various detergent ingredients may deposit onto a fabric, particularly when the fabric is washed in water having metal ions and/or a certain hardness. Treating such a prewashed fabric with treatment composition according to the present disclosure can result in deeper, more vibrant colors or darker darks. Thus, the fabric's colors are "rejuvenated" or restored more closely to the original color of the fabric before washing. Even if the fabric is not fully restored to its original color, the color change can reduce signs of wear and extend the life of the fabric.

The present disclosure also relates to the use of a treatment liquor to rejuvenate a non-white color a fabric, wherein the fabric comprises a metal-based residue (preferably the result of having been previously washed with a laundry detergent and/or treated with hard water), wherein the treatment liquor comprises water and from about 100 ppm to about 20000 ppm of an organic acid, wherein the organic acid is not acetic acid, preferably wherein the organic acid is citric acid, lactic acid, malic acid, maleic acid, salts thereof, or mixtures thereof, more preferably citric acid, salts thereof, or mixtures thereof, preferably wherein the treatment liquor is formed by diluting a treatment composition with water, wherein the treatment composition comprises the organic acid.

Other color rejuvenation methods are known for use on fabrics, but they may require the use of polymers, which can be expensive and/or synthetic. A further benefit of the presently described use is that the compositions described herein may primarily, or even exclusively, include naturally derived ingredients.

The fabric may have been previously washed with a laundry detergent, thereby being a "prewashed fabric." The prewashed fabric may have been previously treated with a laundry detergent in one or more wash cycles, preferably at least two, or at least three, or at least 5, or at least 8, or at least 10 wash cycles. The more times a fabric has been treated by a laundry detergent, the more residue is likely to be deposited on the fabric, and thus the fabric may be in greater need of color rejuvenation. The laundry detergent may be a liquid detergent, a powdered detergent, or a mixture thereof, preferably a powdered detergent. Powdered detergents may be preferred as they may provide relatively more residues than liquid detergents, such as carbonate or silicate salts.

The prewashed fabric may have been treated with water comprising metal ions. The metal ions may be selected from the group consisting of calcium ions, magnesium ions, copper ions, aluminum ions, or mixtures thereof, preferably calcium ions, magnesium ions, or mixtures thereof, more preferably calcium ions. The metal ions may interact with components of laundry detergent and form metal-based residues that deposit on the fabric. The water used to treat the prewashed fabric may be characterized by a hardness of from about 0 to about 30 grains per gallon (gpg), or from about 1 to about 30 gpg, or from about 2 to about 30 grains per gallon, or from about 5 to about 20 gpg, or from about 5 to about 15 gpg, or from about 5 to about 10 gpg. The water may include from about 15 to about 200 ppm calcium, or from about 20 to about 175 ppm calcium, or from about 50 to about 100 ppm calcium. The water may include calcium and magnesium present in a weight ratio of from about 2:1 to about 5:1, or from about 3:1 to about 4:1.

The fabric may comprise a non-white color, which may also exclude near-white colors such as off-white, ivory, cream, beige, and the like. The color may be a relatively dark color, such as black, gray, or blue. The fabric may comprise cotton fibers, poly-cotton fibers, or combinations thereof. The fabric may be denim; the fabric may be a denim garment, such as medium-to-dark-colored jeans, for example those sold under the brand name of LEVI'S®. The treatment compositions of the present disclosure may be particularly useful on such fabrics because the residues deposited thereon are likely to dull the original color or make the fabrics appear faded; the color rejuvenation effect may be less noticeable on lighter-colored or white fabrics. It is noted that many references discourage users from using lemon juice, which contains citric acid, on dark fabrics, as citric acid is known to have a bleaching effect on some fabrics.

As described in more detail below, the treatment composition may comprise an organic acid. The treatment composition may comprise from about 5% to about 50%, by weight of the treatment composition, of the organic acid, with the proviso that if the organic acid is acetic acid in the presence of no other organic acid, then the treatment composition comprises from 10% to about 50%, by weight of the treatment composition, of the acetic acid.

The organic acid may be selected from citric acid, lactic acid, acetic acid, malic acid, maleic acid, salts thereof, or mixtures thereof, preferably citric acid, acetic acid, salts thereof, or mixtures thereof, more preferably at least citric acid and optionally acetic acid. Such organic acids may be preferred as they are readily obtained from naturally derived sources and may be viewed as environmentally friendly, non-synthetic, and/or non-toxic.

The treatment composition may be diluted with water to form a treatment liquor, preferably diluted 100-fold to 1000-fold, more preferably 200-fold to 800-fold. The dilution step may preferably occur in an automatic washing machine, as automatic operations are generally more convenient to the modern user than manual operations. The automatic washing machine may be a top-loading washing machine or a front-loading washing machine, preferably a front-loading washing machine as such machine can conveniently fit under a countertop and typically use less water than a traditional top-loading washing machine. The dilution may occur in a vessel that is not a washing machine, such as a bucket or a tub; such vessels may be preferred if there is to be a soaking period.

The treatment liquor may comprise from about 100 ppm (parts per million) to about 20,000 ppm, or from about 100 ppm to about 10,000 ppm, or from about 100 ppm to about 5000 ppm, or from about 100 to about 1000 ppm, or from about 150 ppm to about 750 ppm, of the organic acid as supplied by the treatment composition. Put another way, the treatment composition, which comprises an organic acid, may be diluted with water in such amounts that the resulting treatment liquor comprises from about 100 ppm (parts per million) to about 20,000 ppm, or from about 100 ppm to about 10,000 ppm, or from about 100 ppm to about 5000 ppm, or from about 100 to about 1000 ppm, or from about 150 ppm to about 750 ppm, of the organic acid.

The fabric may be contacted with the treatment liquor. The contacting step may occur during a wash cycle or a rinse cycle of an automatic washing machine, preferably during a rinse cycle. The contacting step may be preferred in the rinse cycle so that precipitates or residues formed during the wash cycle (e.g., from metal-sensitive detergent components and metal in the wash water) may be removed, at least partially, in addition to residues that deposited during previous wash cycles.

The treatment liquor may be characterized by a temperature of from about 5° C. to about 50° C., or from about 5° C. to about 40° C., or from about 5° C. to about 30° C., or from about 10° C. to about 25° C., or even from about 10° C. to about 20° C. Treatment cycles with relatively cold water may be preferred for energy savings. Furthermore, residues or precipitates are less likely to dissolve on their own at cooler temperatures, meaning that the treatment compositions of the present disclosure may be even more useful at such temperatures.

The difference between the second color and the first color may be measured and reported on the CIE L*a*b* color space models, as described in the test methods below. The L* value of the second color may be less (e.g., closer to black) than the L* value of the first color (e.g., closer to black). For example, the delta-L* value ($L^*_{second\ color} - L^*_{first\ color}$) may be at least about 2, or at least about 3, or at least about 5, or at least about 8, or at least about 10. Greater differences indicate the second color is darker and/or closer to black to greater degrees. The ΔE value between the second and first colors may be at least 2, or at least 3, or at least 5, or at least 8, or at least 10. The first and second colors may be characterized by a Whiteness Index (WI CIE), determined according to the test methods section below. The WI CIE difference ($WI_{second\ color} - WI_{first\ color}$) may be at least 2, or at least 3, or at least 5, or at least 8, or at least 10. Greater magnitude differences in WI CIE indicate greater differences in whiteness, and negative values indicate the second color is less white/darker.

The ΔE of the original color and the second color (e.g., original color→rejuvenated color) may be less than the ΔE of the original color and the first color (e.g., original color→faded color), for example and preferably less by a difference of at least 1, or at least 2, or at least 3, or at least 4, or at least 5, or at least 6, or at least 7, or at least 8, or at least 9, or at least 10. A smaller ΔE in this context indicate that the color, preferably the second color, is closer to the original (e.g., appears less faded). It is believed that a ΔE value of equal to or greater than 2 is typically noticeable to at least 50% of consumers.

Demonstrations of Color Rejuvenation

As mentioned above, it can be difficult to see the metal-based residues directly with the naked eye, and so many consumers are not aware that they are there. Furthermore, because the residues may slowly build-up over time and multiple wash cycles, consumers may not be aware of the apparent color loss or fading in their fabrics compared to the original color, or they may not appreciate the benefits offered by the present treatment compositions. Therefore, providing a method to illustrate the color rejuvenation benefits of the presently disclosed treatment compositions will be beneficial.

The present disclosure may relate to a process of demonstrating the color-rejuvenation benefits of a treatment composition on a single fabric, preferably a single garment. For example, the present disclosure relates to a process of demonstrating the color-rejuvenation benefits of a treatment composition on a fabric where the process includes the step of providing a fabric. Preferably, the fabric has been previously treated by a laundry detergent; in other words, the fabric may be a "prewashed fabric." The prewashed fabric may have been previously treated with a laundry detergent in one or more wash cycles, preferably at least two, or at least three, or at least 5, or at least 8, or at least 10 wash cycles.

The fabric may have a first color, preferably where the color is not white. The color may be a non-white color, which may also exclude near-white colors such as off-white, ivory, cream, beige, and the like. The color may be a relatively dark color. Such colors are more likely to show a greater degree of relative fading due to residue deposition, and a greater degree of color rejuvenation. The color may be black, gray, or blue, preferably black to provide the greatest degree of contrast.

The process may comprise the step of contacting the fabric with a treatment composition, optionally in the presence of water. The treatment composition may comprise from about 5% to about 50%, by weight of the treatment composition, of an organic acid, with the proviso that if the organic acid is acetic acid in the presence of no other organic acid, then the treatment composition comprises from 10% to about 50%, by weight of the treatment composition, of the acetic acid. Preferably the organic acid is selected from citric acid, lactic acid, acetic acid, malic acid, maleic acid, salts thereof, or mixtures thereof, preferably citric acid, acetic acid, salts thereof, or mixtures thereof, more preferably at least citric acid and optionally acetic acid. Such organic acids may be preferred as they are readily obtained from naturally derived sources and may be viewed as environmentally friendly, non-synthetic, and/or non-toxic. Suitable treatment compositions are described in more detail below.

Following treatment with the treatment composition, the fabric may comprise a second color, preferably where the second color is a non-white color, which may also exclude near-white colors such as off-white, ivory, cream, beige, and the like. The second color is different, preferably darker, than the first color.

The process may further comprise the step of displaying a comparison of the first color and second color. The comparison may be a visual display, for example with pictures, photographs, videos, illustrations, or even the actual fabric. The comparison may comprise a first visual representation of the first color, and a second visual representation of the second color. The first and second visual representations may be, respectively, photographs or videos of the fabric's first color before, and the fabric's second color after, treatment with the treatment composition. Typically, the first and second colors are compared at approximately the same location on the fabric, so that the before-and-after comparison can be more easily characterized. If the comparison is made at different locations of the fabric, variations in color may occur that would affect the comparison.

The difference between the second color and the first color may be measured and reported on the CIE L*a*b* color space models, as described in the test methods below. The L* value of the second color may be less (e.g., closer to black) than the L* value of the first color (e.g., closer to black). For example, the delta-L* value ($L^*_{second\ color} - L^*_{first\ color}$) may be at least about 2, or at least about 3, or at least about 5, or at least about 8, or at least about 10. Greater differences indicate the second color is darker and/or closer to black to greater degrees. The ΔE value between the second and first colors may be at least 2, or at least 3, or at least 5, or at least 8, or at least 10. The first and second colors may be characterized by a Whiteness Index (WI CIE), determined according to the test methods section below. The WI CIE difference ($WI_{second\ color} - WI_{first\ color}$) may be at least −2, or at least −3, or at least −5, or at least −8, or at least −10. Greater magnitude differences in WI CIE indicate greater differences in whiteness, and negative values indicate the second color is less white and/or is darker.

The first and second colors may be compared, for example, on the difference from an original color of the fabric, using the same measurements and values as described above. As used herein, the term "original color" means a color of the fabric when new, prior to being treated with a laundry detergent (e.g., prior to being prewashed) by a consumer. The original color of the fabric could mean the color of a new fabric, prior to any washes or wears by a consumer—e.g., the color of the fabric on the day it is purchased or otherwise obtained by a consumer. However, the original color of the fabric may also refer to the color of the fabric at a designated time zero, after which the fabric is washed one or more times with a laundry detergent. For example, the first and second colors may be compared by determining the ΔE of the fabric before and after treatment with the treatment composition described herein (e.g., the differences of the first color and the original color, and the difference of the second color and the original color). The ΔE of the original color and the second color may be less than the ΔE of the original color and the first color, for example less by a differences of at least 1, or at least 2, or at least 3, or at least 4, or at least 5, or at least 6, or at least 7, or at least 8, or at least 9, or at least 10. Greater ΔE in this context indicate that the second color is closer to the original color to a greater degree (e.g., appears less faded).

The present disclosure may relate to a process of demonstrating the color-rejuvenation benefits of a treatment composition on more than one fabric, such as a first fabric and a second fabric, preferably a first garment and a second garment. For example, the present disclosure relates to a process of demonstrating the color-rejuvenation benefits of a treatment composition that comprises the step of providing a first fabric and a second fabric.

The first and second fabrics each comprise an identical original color. As described above, the original color may be the color of the fabrics on the day of purchase, at a time prior to wash or wear, or at a designated time zero. The first fabric comprises a first location comprising the original color. The second fabric comprises a second location comprising the original color. The second location on the second fabric may substantially correspond to the first location on the first fabric. For example, if the first and second fabrics are substantially similar or even identical garments, the first and second locations may be at corresponding positions on the respective garments, such as on a right shoulder area or a left rear pocket. If the first and second fabrics comprise multiple colors, for example in patterns that do not exactly correspond, the first and second locations on the fabrics should be selected so that identical original colors (e.g., both black) are being compared, even if the locations do not exactly correspond to each other. For some fabrics, the first and second locations may be substantially the entire first and second fabrics, respectively, for example if the fabric is mostly or entirely one color.

It is preferred that the original color is a non-white color (which may also exclude the near-white colors, etc., mentioned above) so that the color rejuvenation effects can be demonstrated more effectively. Darker colors may be preferred, such as black, gray, or blue.

The process may comprise the step(s) of washing the first and second fabrics with a laundry detergent composition one or more times under substantially identical conditions. The washing step(s) may take place in one or more automatic washing machines, preferably in the same washing machine, more preferably at the same time. By "substantially identical conditions," it is meant that the fabrics undergo substantially similar wash cycles, including, for example, same wash time, water temperature, cycle agitation, ballast, detergent dosage, rinse and drying conditions, etc. The fabrics may be washed with a laundry detergent in one or more wash cycles, preferably at least two, or at least three, or at least 5, or at least 8, or at least 10 wash cycles. The more times a fabric has been treated by a laundry detergent, the more residue is likely to be deposited on the fabric, and thus the fabric may be in greater need of color rejuvenation, and the color change resulting from treatment with the present treatment compositions will be more evident. The fabrics may be washed in water having a certain level of hardness and/or metal ions, as described herein. Additionally or alternatively, the process may comprise the step of providing a first and second fabric that has undergone one or more identical wash cycles that includes treating the fabrics with a laundry detergent. After being washed as described herein, it is expected that the colors of the first and second fabrics at the first and second locations, respectively, will appear faded or duller compared to the original color. It is also expected that because the fabrics were treated/washed under substantially identical conditions, the colors at the first and second locations will be substantially similar at this point.

Once the first and second fabrics have been treated and/or provided, the process further comprises treating the second fabric, but not the first fabric, with a treatment liquor, the treatment liquor comprising an organic acid. The organic acid may be added directly to water to form the treatment liquor. Preferably, the treatment liquor is formed by combining water and a treatment composition, where the treatment composition is the source of the organic acid. Suitable organic acids and treatment compositions are more fully described herein. The step of treating the second fabric with a treatment liquor may preferably occur in an automatic washing machine, preferably during a rinse cycle. The fabrics may be dried, for example by line drying or by an automatic dryer machine.

After treatment of the second fabric with the treatment liquor, the process may comprise the step of displaying a post-treatment color comparison of the first fabric and the second fabric. The post-treatment color comparison may comprise a visual comparison. The comparison may be a visual display, for example with photographs, videos, illustrations, or even the actual fabrics. For example, the first and second fabrics may be displayed next to each other or sequentially, or photos or videos of each fabric may be provided side-by-side or sequentially, preferably side-by-side to allow simultaneous comparison.

It may be preferred that the post-treatment color comparison includes a comparison, preferably a visual comparison, of the first location on the first fabric with the second location on the second fabric. The first location may be characterized by a first color. The second location may be characterized by a second color. The first color may be different than the second color. Preferably, the second color is relatively darker than the first color, and/or the second color is relatively closer to the original color than the first color is. This may be because after treatment with the treatment liquor comprising an organic acid, the second fabric's colors have been rejuvenated after having been washed with a laundry detergent as described herein.

Without being bound by theory, it is believed that residues, such as metal-based residues that may in part be derived from laundry detergent ingredients, deposit on the fabrics during the wash cycle(s) and dull the fabric color, whereas the treatment liquor and/or treatment compositions according to the present disclosure, which include organic acids, remove the residue, resulting in darker or brighter fabric colors.

Displaying the fabric, including the corresponding first and second locations of the fabrics after the described treatment regimen can usefully highlight the color rejuvenation benefits of the treatment liquors and/or treatment compositions described herein.

The post-treatment color comparison may comprise a comparison of the colors (e.g., the first and second colors) on one or more vectors of the well-known L*a*b* color scale. The first and second colors may be compared, for example, to each other, or based on the difference of each from the original color of the fabric.

Throughout the present disclosure, the processes generally include one or more washing or treatment steps, where a fabric is treated with a laundry detergent, which can result in residue build-up on the fabrics. The present disclosure further contemplates simulations of such treatment or wash cycles, in which residues, such as metal-based residues are added directly or indirectly to fabrics. For example, a fabric, or an aqueous composition used to contact the fabric, may be doped with such residues, such as metal-based residues (e.g., calcium carbonates, or calcium salts of anionic surfactants). Additionally or alternatively, fabrics may be treated in mini-washers rather than full-scale machines, or even in beakers. Such simulations may be desired to save time or water, or to ensure consistency of residue deposition across fabrics or trials. In the present disclosure, such wash cycle simulations may be substituted for traditional washing cycles (e.g., where a fabric is described as being "pre-washed," the fabric may be treated with a simulated wash process instead), so long as the simulation allows for possible residues to deposit onto the fabric.

Treatment Composition

As described above, the present disclosure relates to processes and uses that employ a treatment composition that comprises an organic acid.

The treatment composition may be a liquid. The liquid composition may be of relatively low viscosity, even similar to that of water. Consumers may desire such low-viscosity compositions due to an association with purity, natural-ness, and/or simplicity. The compositions may be characterized by a viscosity of from about 1 to about 200, or to about 150, or to about 100, or to about 75 cps, or to about 50 cps, or to about 30 cps, or to about 20 cps, or to about 15 cps, or to about 10 cps. As used herein, viscosity is determined by the method provided in the Test Methods section below.

The treatment compositions of the present disclosure may be acidic compositions. The treatment compositions of the present disclosure may be characterized by a pH of less than 7, or less than about 6, or less than about 5, or less than about 4, or less than about 3. The treatment compositions of the present disclosure may be characterized by a pH of from about 1, or from about 1.5, or from about 2, to about 6, or to about 5, or to about 4, or to about 3, or to about 2.5. The compositions may have a pH of from about 2 to about 3.

In addition to the organic acids described below, the treatment compositions may comprise additional pH adjusting agents, such as buffer agents and/or neutralizing agents, such as caustic materials (e.g., NaOH).

The treatment compositions of the present disclosure may be characterized by a Reserve Acidity measurement. Without being limited by theory, the Reserve Acidity measurement is found to be the best measure of the acidifying power of a composition, or the ability of a composition to provide a target acidic wash or rinse pH when added at high dilution into tap water as opposed to pure or distilled water. The Reserve Acidity may be controlled by the level of formulated organic acid along with the neat product pH as well as, in some aspects, other buffers. The treatment compositions of the present disclosure may have a Reserve Acidity to pH 4.0, or even 4.00, of at least about 1, or at least about 3, or at least about 5. The treatment compositions described may have a Reserve Acidity to pH 4.0 of from about 3 to about 10, or from about 4 to about 7. As used herein, "Reserve Acidity" refers to the grams of NaOH per 100 g of product required to attain a pH of 4.0, or even 4.00. The Reserve Acidity measurement as used herein is based upon titration (at standard temperature and pressure) of a 1% product solution in distilled water to an end point of pH 4.0, or even 4.00, using standardized NaOH solution.

The treatment compositions of the present disclosure may be substantially transparent. Such compositions may signal purity and/or natural origins (and consequently, lack of synthetic ingredients) to the consumer. The treatment compositions may be characterized by a percent transmittance (% T) of at least about 50%, or at least about 60%, or at least about 70%, or at least about 80%, or at least about 90%, or at least about 95% of light using a 1 centimeter cuvette, at a wavelength of 410-800 nanometers, or 570-690 nanometers, where the composition is substantially free of dyes. For purposes of this disclosure, as long as one wavelength in the visible light range has greater than 50% transmittance, it is considered to be substantially transparent/translucent.

The disclosed treatment compositions may be isotropic at 22° C. As used herein, "isotropic" means a clear mixture, having a % transmittance of greater than 50% at a wavelength of 570 nm measured via a standard 10 mm pathlength cuvette with a Beckman DU spectrophotometer, in the absence of dyes. The percent transmittance is determined according to the method provided in the Test Methods section below.

Alternatively, transparency of the treatment composition may be measured as having an absorbency in the visible light wavelength (from about 410 to 800 nm) of less than 0.3, which is in turn equivalent to at least 50% transmittance using the cuvette and wavelengths noted above.

The treatment composition may comprise an organic acid, preferably citric acid, typically at a relatively high level. The treatment composition may comprise from about 5% to about 50%, by weight of the treatment composition, of the organic acid, preferably citric acid, with the proviso that if the organic acid is acetic acid in the presence of no other organic acid, then the treatment composition comprises from 10% to about 50%, by weight of the treatment composition, of the acetic acid. The treatment composition may comprise from about 10% to about 50%, or from about 15% to about 40%, or from about 20% to about 30%, by weight of the treatment composition, of the organic acid. The treatment composition may comprise at least about 5%, or at least about 10%, or at least about 15%, or from about 18%, or from about 20%, or from about 22%, or from about 25%, to about 50%, or to about 45%, or to about 40%, or to about 35%, or to about 30%, or to about 28%, or to about 25%, by weight of the composition, of an organic acid. The treatment composition may comprise at least about 15%, or at least about 18%, or at least about 20%, or at least about 22%, or at least about 25%, by weight of the composition, of an organic acid.

A compound's affinity for particular metal ions can be described in terms of a binding constant, which are known and published for common compounds. The organic acid may have a binding constant (log Ki) for calcium ions ($Ca^{2+}$) of at least about 2.5, or at least about 3.0, or at least about 3.5. Magnesium ion ($Mg^{2+}$) can also contribute to water hardness, and the metal sequestration agent may have a binding constant magnesium ions of at least about 2.0, or at least about 2.5.

The organic acid may be selected from citric acid, lactic acid, acetic acid, malic acid, maleic acid, salts thereof, or mixtures thereof, preferably citric acid, acetic acid, salts thereof, or mixtures thereof, more preferably at least citric acid and optionally acetic acid. Such organic acids may be preferred as they are readily obtained from naturally derived sources and may be viewed as environmentally friendly, non-synthetic, and/or non-toxic.

The organic acid may be naturally derived. The organic acid may be substantially biodegradeable for environmental/sustainability reasons. Biodegradeability may be determined by the Sturm Ready Biodegradeability Test.

Citric acid is the preferred organic acid for use in the treatment compositions of the present disclosure, for at least environmental, cost, sequestration efficiency reasons, and/or acidification capabilities.

The treatment compositions of the present disclosure may contain an additional organic acid. Such acids may facilitate pH control and/or treatment benefits. The additional organic acid may be selected from acetic acid, lactic acid, adipic acid, aspartic acid, carboxymethyloxymalonic acid, carboxymethyloxysuccinic acid, glutaric acid, hydroxyethyliminodiacetic acid, iminodiacetic acid, maleic acid, malic acid, malonic acid, oxydiacetic acid, oxydisuccinic acid, succinic acid, sulfamic acid, tartaric acid, tartaric-discuccinic acid, tartaric-monosuccinic acid, or mixtures thereof, preferably acetic acid.

Acetic acid may be added to the composition, or present in the composition, in the form of vinegar. Thus, the compositions of the present disclosure may comprise acetic acid and/or vinegar. Acetic acid and/or vinegar may be preferred for traditional fabric care benefits associated with vinegar, including softness and/or cleaning. Acetic acid may be present at a level of from about 0.05%, or from about 0.1%, or from about 0.15%, or from about 0.2% to about 5%, or to about 3%, or to about 2%, or to about 1%, or to about 0.5%, or to about 0.3%, by weight of the composition. Vinegar may be present at a level of from about 0.5%, or from about 1%, or from about 1.5%, or from about 2%, to about 20%, or to about 15%, or to about 10%, or to about 5%, or to about 4%, or to about 3%, by weight of the composition.

The compositions of the present disclosure may include a biodegradeable organic acid, such as citric acid, in combination with acetic acid/vinegar, as such a combination provides sustainable ingredients that are perceived as natural or safe by many consumers. The organic acid, preferably citric acid, and acetic acid may be present in a weight ratio of from about 300:1, or from about 250:1, or from about 225:1, or from about 200:1, to about 1:1, or to about 10:1, or to about 50:1, or to about 100:1. It may be desirable to have relatively more of organic acid (e.g., citric acid) compared to the acetic acid in order to improve performance while minimizing undesirable odor that is often associated with acetic acid/vinegar. Due to the odor of acetic acid/vinegar, it may even be preferred that the treatment composition is substantially free, or even completely free, of acetic acid and/or vinegar.

The treatment compositions are typically aqueous compositions. Thus, the treatment compositions may comprise water. The treatment compositions of the present disclosure may comprise from about 30%, or from about 40%, or from about 50%, to about 95%, or to about 90%, or to about 80%, or to about 75%, or to about 70%, by weight of the fabric composition, of water.

Although the treatment compositions of the present disclosure are aqueous, the compositions may further comprise organic solvent, which can improve composition stability, ingredient dissolution, and/or transparency of the composition. The treatment compositions may include from about 0.1% to about 30%, or from about 1% to about 20%, by weight of the composition, of organic solvent. Suitable organic solvents may include ethanol, diethylene glycol (DEG), 2-methyl-1,3-propanediol (MPD), monopropylene glycol (MPG), dipropylene glycol (DPG), oligamines (e.g., diethylenetriamine (DETA), tetraethylenepentamine (TEPA)), glycerine, propoxylated glycerine, ethoxylated glycerine, ethanol, 1,2-propanediol (also referred to as propylene glycol), 1,3-propanediol, 2,3-butanediol, cellulosic ethanol, renewable propylene glycol, renewable monopropylene glycol, renewable dipropylene glycol, renewable 1,3-propanediol, and mixtures thereof. One or more of the organic solvents may be bio-based, meaning that they are derived from a natural/sustainable, non-geologically-derived (e.g., non-petroleum-based) source.

The treatment compositions of the present disclosure may comprise perfume. Perfume may provide a signal to the user that a fabric treated with the composition is now clean. Perfume may also serve to mask undesirable odors of other components of the composition, such as acetic acid.

The treatment compositions of the present disclosure may comprise a limited number of ingredients, for example, no more than ten, or no more than nine, or no more than eight, or no more than seven, or no more than six, or no more than five ingredients. Limiting the number of ingredients can result in lower storage and/or transportation costs of raw materials, and/or simplify the process of making the compositions. Consumers may also desire products having a limited number of ingredients, as they may be perceived as simpler, as having a smaller environmental footprint, and/or as providing an easier-to-understand ingredient list. The treatment compositions of the present disclosure may consist essentially of, or even consist of, the desired components.

As described above, the present treatment compositions may be relatively transparent. Therefore, the present treatment composition may be substantially free of particles, such as encapsulated benefit agents, silicone droplets, pearlescent agents, and/or opacifiers, which may reduce the relative transparency of the composition. The present treatment compositions may be substantially free of dyes. As used herein the term "dye" includes aesthetic dyes that modify the aesthetics of the cleaning composition as well as dyes and/or pigments that can deposit onto a fabric and alter the tint of the fabric. Dyes may include colorants, pigments, and hueing agents. The present treatment compositions may be free of optical brighteners.

The present treatment compositions may be substantially free of detersive surfactant (such as anionic, nonionic, amphoteric, and/or zwitterionic surfactants, although small amounts of nonionic surfactant may be present, for example to aid with perfume incorporation or product stability), bleaching systems (such as peroxide and/or hypohalite bleaches), and/or fabric softening actives ("FSAs", such as quaternary ammonium ester compounds and/or silicones). Such materials may affect the aesthetics, physical stability, and/or chemical stability of the other ingredients in the present compositions. Additionally or alternatively, certain such materials may not be physically or chemically stable themselves in low-pH environment of the present compositions. Furthermore, consumers who use the present compositions may be hoping to remove materials from their treated fabrics, whereas at least some of the listed materials may instead deposit on fabric during a normal treatment cycle, building up undesirable residues. Fabric softening actives may include quaternary ammonium ester compounds, silicones, non-ester quaternary ammonium compounds, amines, fatty esters, sucrose esters, silicones, dispersible polyolefins, polysaccharides, fatty acids, softening or conditioning oils, polymer latexes, or combinations thereof. As used herein, the terms "fabric softening actives" is not intended to include any of the materials listed above as metal sequestration agents and/or additional organic acids, including vinegar or acetic acid.

In an effort to keep viscosity low, the treatment compositions of the present disclosure may be substantially free of thickeners or other rheology enhancers, such as structurants. The treatment compositions may be substantially free of salts, such as inorganic salts like sodium chloride, magnesium chloride, and/or calcium chloride, that can provide rheology modification such as thickening. As used herein, such salts are not intended to include the neutralization products of the organic acids described herein.

The treatment composition may be provided in any suitable container, including those constructed from paper, cardboard, plastic materials, and any suitable laminates. The container may contain sustainably sourced, renewable, and/or recyclable materials. The container may be made of translucent or even transparent materials, such as translucent or transparent plastic. Such container types may preferred in order to provide visual communication between the consumer and the treatment composition, for example to determine the remaining volume of composition in the container.

Combinations

Specifically contemplated combinations of the disclosure are herein described in the following lettered paragraphs. These combinations are intended to be illustrative in nature and are not intended to be limiting.

A. A process to determine the presence of a metal-based residue on a fabric, the process comprising the steps of: providing a vessel with a storage portion and an open mouth; providing a treatment liquor to the storage portion of the vessel, the treatment liquor comprising an organic acid, optionally, forming the treatment liquor by combining a treatment composition and water, the treatment composition comprising the organic acid; submerging at least a portion of a fabric in the treatment liquor for at least two seconds; and detecting the presence of released residue in the treatment liquor.

B. A use of a treatment composition to rejuvenate a non-white color of a fabric, wherein the fabric has been previously washed with a laundry detergent, wherein the treatment composition comprises an organic acid, wherein the treatment composition is diluted with water to form a treatment liquor, preferably diluted from about 100-fold to about 1000-fold, preferably in an automatic washing machine, more preferably during a rinse cycle, and wherein the fabric is contacted with the treatment liquor, further wherein at least one of the following is true: (a) the treatment composition comprises from about 5% to about 50%, by weight of the treatment composition, of the organic acid, with the proviso that if the organic acid is acetic acid in the presence of no other organic acid, then the treatment composition comprises from 10% to about 50%, by weight of the treatment composition, of the acetic acid; or (b) the treatment liquor comprises from about 100 ppm to about 20000 ppm, or from about 100 ppm to about 10,000 ppm, or from about 100 ppm to about 5000 ppm, or from about 100 to about 1000 ppm, or from about 150 ppm to about 750 ppm, of the organic acid as supplied by the treatment composition, wherein the organic acid is not acetic acid.

C. A use of a treatment liquor to rejuvenate a non-white color of a fabric, wherein the fabric comprises a metal-based residue, wherein the treatment liquor comprises water and from about 100 ppm to about 20000 ppm, or from about 100 ppm to about 10,000 ppm, or from about 100 ppm to about 5000 ppm, or from about 100 to about 1000 ppm, or from about 150 ppm to about 750 ppm, of an organic acid, wherein the organic acid is not acetic acid, preferably wherein the organic acid is citric acid, lactic acid, malic acid, maleic acid, salts thereof, or mixtures thereof, more preferably citric acid, salts thereof, or mixtures thereof, preferably wherein the treatment liquor is formed by diluting a treatment composition with water, more preferably a dilution of from about 100-fold to about 1000-fold, wherein the treatment composition comprises the organic acid.

D. The use according to any of paragraphs B or C, wherein the fabric is characterized by: an original color when new; a first color when faded, preferably faded as a result of having been previously washed with a laundry detergent; and a second color following treatment with the treatment liquor; where the difference in color ($\Delta E$) between of the original color and the second color is less than the difference in color ($\Delta E$) between the original color and the first color.

E. A process to demonstrate the color-rejuvenation benefits of a treatment composition, the process comprising the steps of: providing a fabric, the fabric having been previously treated by a laundry detergent, the fabric having a first color, wherein the first color is a non-white color; contacting the fabric with the treatment composition, optionally in the presence of water, wherein the treatment composition comprises from about 5% to about 50%, by weight of the treatment composition, of an organic acid, with the proviso that if the organic acid is acetic acid in the presence of no other organic acid, then the treatment composition comprises from 10% to about 50%, by weight of the treatment composition, of the acetic acid; the fabric having a second color following treatment with the treatment composition, wherein the second color is a non-white color; and displaying a post-treatment comparison of the first color and the second color.

F. A process to demonstrate the color-rejuvenation benefits of a treatment composition, the process comprising the steps of: providing a first fabric and a second fabric, the first and second fabrics comprising an identical first color, wherein the first color is a non-white color; the first fabric comprising a first location comprising the first color, the second fabric comprising a second location comprising the first color, wherein the second location of second fabric substantially correlates to the first location of the first fabric; washing the first and second fabrics with a laundry detergent composition one or more times under substantially identical conditions; treating the second fabric, but not the first fabric, with a treatment liquor, the treatment liquor comprising an organic acid, wherein the treatment liquor is optionally formed by combining water and a treatment composition, the treatment composition being the source of the organic acid; and then displaying a post-treatment color comparison of the first fabric and the second fabric.

G. The process or use of any of paragraphs A-F, wherein the organic acid is selected from the group consisting of citric acid, acetic acid, lactic acid, malic acid, maleic acid, salts thereof, and mixtures thereof; preferably citric acid, acetic acid, salts thereof, and mixtures thereof.

H. The process or use of any of paragraphs A-G, wherein the organic acid is citric acid, a salt thereof, or a mixture thereof.

I. The process or use of any of paragraphs A-H, wherein the organic acid is a naturally derived organic acid.

J. The process or use of any of paragraphs A-I, wherein the fabric comprises a metal-based residue, preferably wherein the metal is calcium, magnesium, copper, aluminum, or mixtures thereof, more preferably calcium, magnesium, or mixtures thereof, more preferably calcium.

K. The process or use of any of paragraphs A-J, wherein the fabric, the first fabric, or the second fabric, if present, was prewashed with a powdered laundry detergent.

L. The process or use of any of paragraphs A-K, wherein the prewashed fabric has been treated with a laundry detergent in at least two wash cycles, preferably at least three, preferably at least five, preferably at least eight, preferably at least ten wash cycles.

M. The process or use of any of paragraphs A-L, wherein the fabric, the first fabric, or the second fabric, if present, was prewashed in water having a hardness of from about 0 to about 30 grains per gallon (gpg), or from about 1 to about 30 gpg, or from about 2 to about 30 grains per gallon, preferably from about 5 to about 20 gpg, or from about 5 to about 15 gpg, or from about 5 to about 10 gpg.

N. The process or use of any of paragraphs A-M, wherein the treatment composition comprises from about 5% to about 50%, preferably from about 10% to about 50%, more preferably from about 15% to about 40%, even more preferably from about 20% to about 30%, by weight of the treatment composition, of the organic acid, with the proviso that if the organic acid is acetic acid in the presence of no other organic acid, then the treatment composition comprises from 10% to about 50%, by weight of the treatment composition, of the acetic acid.

O. The process or use of any of paragraphs A-N, wherein the first color and the second color are characterized by at least one of the following, based on the CIE L*a*b* color space:
(a) wherein the delta-L* value ($L*_{second\ color} - L*_{first\ color}$) is at least about 2, or at least about 3, or at least about 5, or at least about 8, or at least about 10; or
(b) wherein the ΔE value between the second and first colors is at least 2, or at least 3, or at least 5, or at least 8, or at least 10; or
(c) wherein the WI CIE difference ($WI_{second\ color} - WI_{first\ color}$) is at least 2, or at least 3, or at least 5, or at least 8, or at least 10; or
(d) wherein the first and second fabrics are characterized by an original color, and wherein the difference in color (ΔE) between the original color and the second color is less than the difference in color (ΔE) between the original color and the first color, preferably less by a difference of at least 1, or at least 2, or at least 3, or at least 4, or at least 5, or at least 6, or at least 7, or at least 8, or at least 9, or at least 10; or
(e) combinations thereof.

P. The process or use of any of paragraphs A-O, wherein the fabric comprises cotton fibers, polycotton fibers, or combinations thereof.

Q. The process or use of any of paragraphs A-P, wherein the fabric comprises a plurality of colors.

R. The process of any of paragraphs E-Q, wherein the step of displaying a post-treatment comparison of the first color and the second color comprises displaying a visual comparison, preferably where visual representations are provided side-by-side or sequentially, preferably side-by-side.

S. The process or use of any of paragraphs A-R, wherein the metal-based residue is derived from an anionic surfactant, an anionic polymer, a carbonate, a silicate, or a combination thereof.

T. The process or use of any of paragraphs A-S, wherein the metal-based residue is derived from a laundry detergent.

U. The process of any of paragraphs A or E-T, wherein the first and/or second fabric is characterized by: an original color when new; a first color when faded, preferably faded as a result of having been previously washed with a laundry detergent; and a second color following treatment with the treatment liquor; where the difference in color (ΔE) between of the original color and the second color is less than the difference in color (ΔE) between the original color and the first color.

Test Methods

Water Hardness

Water hardness is measured using test strips (Sofchek water quality test strips, HACH Company, Loveland, Colo.). Water is tested prior to being combined with a detergent or treatment composition. For each measurement, a 40 mL water aliquot is removed and pH is measured; then hardness is measured by dipping a test strip in water for 1s, shaking off excess water, waiting for 15s, and determining the hardness according to the color scale printed on the package.

Determination of pH

Unless otherwise stated herein, the pH of the composition is defined as the neat pH of the composition at 20±2° C. Any meter capable of measuring pH to ±0.01 pH units is suitable. Orion meters (Thermo Scientific, Clintinpark-Keppekouter, Ninovesteenweg 198, 9320 Erembodegem-Aalst, Belgium) or equivalent are acceptable instruments. The pH meter should be equipped with a suitable glass electrode with calomel or silver/silver chloride reference. An example includes Mettler DB 115. The electrode should be stored in the manufacturer's recommended electrolyte solution. The pH is measured according to the standard procedure of the pH meter manufacturer. Furthermore, the manufacturer's instructions to set up and calibrate the pH assembly should be followed.

Determination of Viscosity

The viscosity of a composition is determined by rotational viscometry using a Brookfield viscometer and the ASTM D 2196-99 at 60 RPM and 22° C.

Transmittance (% T)

As a measurement of the relative transparency/translucency of a composition, the percent transmittance (% T) of the composition may be determined. The percent transmittance of a composition is measured at the desired wavelength a standard 10 mm pathlength cuvette with a Beckman DU spectrophotometer, in the absence of dyes. The machine may be calibrated using a blank cuvette containing deionized water.

Prior to measuring percent transmittance of a sample composition, vigorously shake a jar containing the composition for 10 seconds. Immediately place a sample into a 1-cm cuvette. Vigorously shake the sample in the cuvette for 10 seconds. Wait 30 seconds and measure the percent transmittance.

Turbidity Method

To measure the turbidity of the compositions, the Mettler Toledo FSC402 Process Turbidity Meter is calibrated. Turbidity is measured using a Mettler Toledo FSC402, Process Turbidity Meter using back scattering, or equivalent, which measures relative turbidity from 0 to 100% as described herein. To calibrate this instrument, 100 g white gloss latex paint or equivalent (Everwhite, Non-Yellowing. Low Odour Gloss. Supplied by B&Q, UK) is placed into a 120 ml Beatson Clark Glass Jar (Base diameter; 6 cm, Top diameter; 5.2 cm, Height to Bottom of Screw Lip; 5 cm). The probe is slowly inserted into the paint to minimize formation of air bubbles, ensuring that the top of the probe is 4 cm from the base of the jar. White gloss paint is calibrated as 100% turbidity. Next, the probe is cleaned with ethanol and 10 g DI Water poured into a 120 ml Beatson Clark Glass Jar (base diameter; 6 cm, top diameter; 5.2 cm, height to bottom of screw lip; 5 cm). The probe is inserted slowly into the water, ensuring that the top of the probe is 4 cm from the base of the jar. De-ionised water is calibrated as 0% Turbidity. The probe is cleaned with ethanol after each reading. The "Gain" is recorded each time the instrument is used and it is ensured that this remains constant each time the instrument is used, Calibration is now complete.

All compositions should be stored at 25° C. prior to turbidity readings being taken to minimize error.

In order to measure the change in turbidity in a treatment liquor upon treatment of a fabric/removal of residue, 100 g of the treatment liquor (prior to treating a fabric) is weighed into a 120 ml Beatson Clark Glass Jar (base diameter; 6 cm, top diameter; 5.2 cm, height to bottom of screw lip; 5 cm). The probe is slowly inserted into the composition to minimize formation of air bubbles, ensuring that the top of the probe is 4 cm from the base of the jar. A reading is taken once the display has settled, then a second reading is taken after 60 seconds. An average of these two readings is recorded. Turbidity readings are in % Turbidity.

This procedure is repeated to determine the turbidity of the treatment liquor within five minutes of treating a fabric.

The processes of the present disclosure may be characterized by undergoing a turbidity increase upon treatment of the fabric/removal of the residue of greater than 5%, preferably greater than 10%, more preferably greater than 15%, more preferably still greater than 20%, yet more preferably greater than 25%. For the avoidance of doubt, the percentage turbidity increase is calculated by subtracting the % turbidity value of the treatment liquor alone, from the % turbidity value of the treatment liquor within five minutes of having treated a fabric.

Color Measurements

As used herein and as will be familiar one of ordinary skill, the "L*a*b* color space" is a three dimensional colorimetric model developed by Hunter Associates Laboratory and recommended by the Commission Internationale d'Eclairage ("CIE") to measure the color or change in color of a dyed article. The CIE L*a*b* color space ("CIELAB") has a scale with three-fold axes with the L axis representing the lightness of the color space (L*=0 for black, L*=100 for white), the a* axis representing color space from red to green (a*>0 for red, a*<0 for green) and the b* axis representing color space from yellow to blue (b*>0 for yellow, b*<0 for blue). Term definitions and equation derivations are available from Hunter Associates Laboratory, Inc. and from www.hunterlab.com, and are incorporated in their entirety by reference herein.

Colors may be measured via spectrophotometry, for example, via a Spectrophotomer CM-3610d, manufactured by Konica Minolta, Tokyo, Japan. Values for each L*a*b* axis can be reported individually. At least two L*, a*, and b* measurements are taken for each value per fabric, and the value for each axis is reported as an average.

Differences in colors can be determined directly for any one axis (e.g., $\Delta L^* = L^*_x - L^*_y$). Additionally, an overall color difference ($\Delta E$) can be calculated using L*, a*, and b* values by the formula $\Delta E = [(L^*_x - L^*_y)^2 + (a^*_x - a^*_y)^2 + (b^*_x - b^*_y)^2)^7]^{1/2}$. Color differences may be reported between two fabrics, for example one having been treated with a treatment composition where another fabric has not. Color differences may also be determined between a fabrics "original" color (e.g., at time=0) and the present color (e.g., after a certain treatment).

Relatively higher differences in color values (e.g., $\Delta L^*$ or $\Delta E$ . . . ) correspond to relatively greater degrees of color change. It is believed that a $\Delta E$ value of equal to or greater than 2 is typically noticeable to at least 50% of consumers.

Whiteness Index

As used herein and as will be familiar one of ordinary skill, the "L*a*b* color space" are three dimensional colorimetric models developed by Hunter Associates Laboratory and recommended by the Commission Internationale d'Eclairage ("CIE") to measure the color or change in color of an article. The CIE L*a*b* color space ("CIELAB") has a scale with three-fold axes with the L axis representing the lightness of the color space (L*=0 for black, L*=100 for white), the a* axis representing color space from red to green (a*>0 for red, a*<0 for green) and the b* axis representing color space from yellow to blue (b*>0 for yellow, b*<0 for blue). Term definitions and equation derivations are available from Hunter Associates Laboratory, Inc. and from www.hunterlab.com, and are incorporated in their entirety by reference herein.

The whiteness of a fabric can be described, for example, in terms of Whiteness Index (WI) which is derived from CIE L*a*b* before and after the wash treatment of the fabric as measured via spectrophotometry (for example, via a DU 800 Spectrophotomer, manufactured by Hunter Laboratories, USA) and is reported as a WI value. A difference in WI values includes the vector associated with the distance in the Whiteness Index space (derived via the CIE L*a*b* space between the initial L*a*b* value and the final L*a*b* value).

Relatively higher delta-WI values correspond to a greater Whiteness recovery, indicating that the fabric became more white in color (e.g., lighter). Negative delta-WI indicated that the fabric become less white in color (e.g., darker).

EXAMPLES

The examples provided below are intended to be illustrative in nature and are not intended to be limiting.

Example 1. Process of Demonstrating Residue Removal (1)

Figure 2:
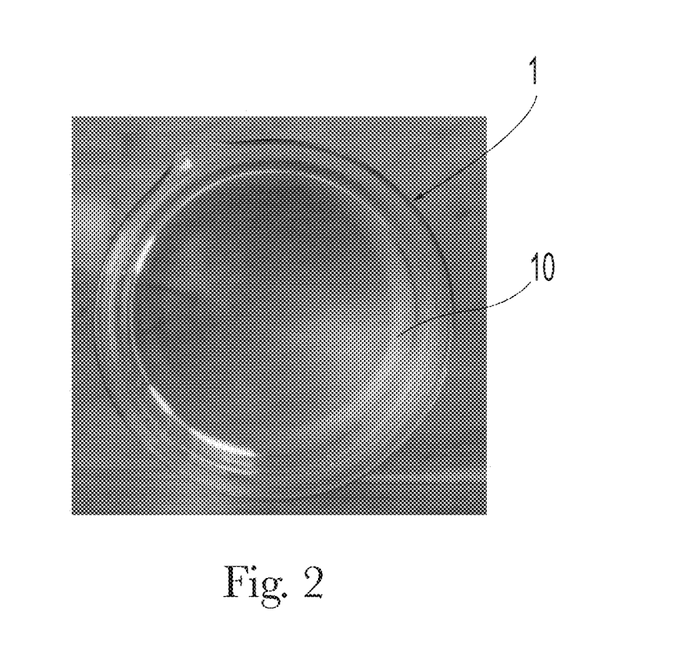
FIG. 2 shows a top view of an exemplary vessel that includes a treatment liquor.
Figure 3:
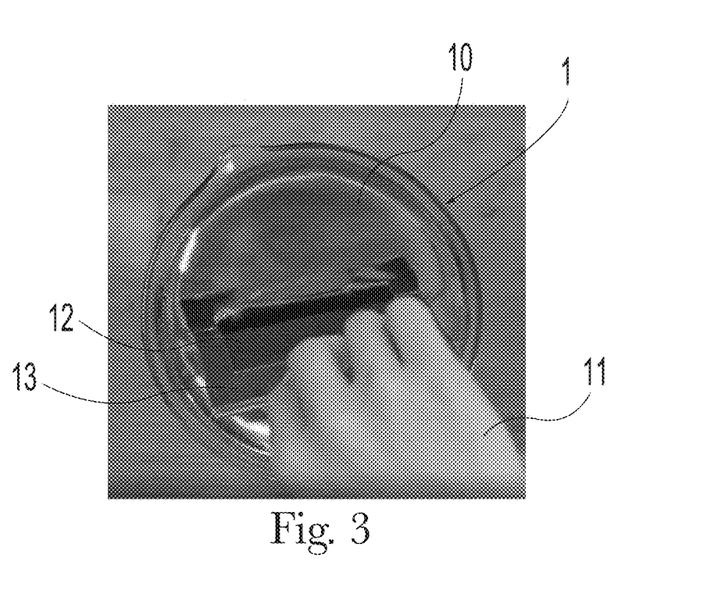
FIG. 3 shows a fabric being provided to the vessel of FIG. 2.
Figure 4:
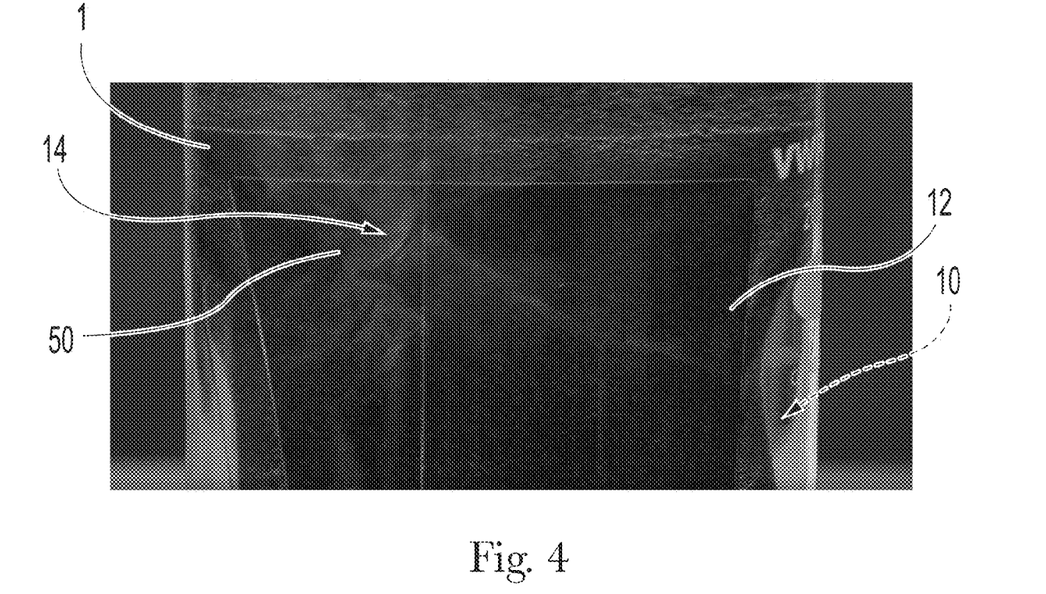
FIG. 4 shows a side view of the vessel of FIG. 2, including a fabric submerged in a treatment liquor.

FIGS. 2-4 show photographic stills from a video showing a process according the present disclosure related to demonstrating residue removal from a fabric.

As shown by a top view in FIG. 2, a vessel 1 (namely a 2 L beaker) is provided. The vessel 1 includes a treatment liquor 10 in the storage volume of the beaker. The treatment liquor 10 is made by providing 1.6 L of water to the vessel 1, and then further providing 80 mL of an acidic treatment composition. The treatment composition includes: about 23.7 wt % citric acid; about 5 wt % organic solvent (propylene diol); about 2 wt % sodium hydroxide; about 0.16 wt % acetic acid (added as vinegar); about 0.5 wt % perfume; and water. The resulting treatment liquor 10 contains about 12000 ppm of citric acid.

As shown in FIG. 3, a fabric 12 is provided by hand 11 to a treatment liquor 10 contained in the vessel 1. The fabric 12 is a black fabric (100% cotton t-shirt) and is stretched taut in a plastic frame 13. Prior to the treatment shown in the figure, the fabric 12 has been washed ten times with a powdered laundry detergent (ARM & HAMMER® plus Oxi Clean Stainfighters) and water characterized by a hardness of 6 gpg.

FIG. 4 shows a side view of the vessel 1, with the fabric 12 submerged in the treatment liquor 10. (The curved wall of the vessel 1 distorts the view of the fabric 12.) The vessel 1 includes a transparent portion 50, namely the side wall of the vessel 1 which is made of a transparent material. At the time the still was captured, the fabric 12 has been submerged for about eleven seconds. The cloudiness 14 shown in the picture in front of the fabric 12 is evidence of residues being released from the fabric as solids and gasses into the treatment liquor. In real time, the residues appear to be moving like wisps of smoke, and the amount of cloudiness 14 increases from the first second to the eleventh.

Example 2. Process of demonstrating residue removal (2)

The demonstration process according to Example 1 is performed, but with the following difference. The treatment liquor is provided by adding 112 mL of the treatment composition described in Example 1 to 1.6 L of water. The resulting treatment liquor contains about 16600 ppm citric acid.

Example 3. Process of Demonstrating Residue Removal (3)

The demonstration process according to Example 1 is performed, but with the following difference. The treatment liquor is provided by adding 80 mL of a treatment composition that is a liquid laundry detergent to 1.6 L of water. The laundry detergent includes: about 6.8 wt % HLAS; about 9.9 wt % nonionic surfactant (NI 24-9); about 14 wt % citric acid; about 3 wt % organic solvent (propylene diol); about 1.3 wt % sodium hydroxide; about 0.09 wt % acetic acid; about 1 wt % perfume; and water (final pH=about 2.5). The resulting treatment liquor contains about 7400 ppm citric acid.

Example 4. Process of Demonstrating Residue Removal (4)

The demonstration process according to Example 1 is performed, but with the following difference. The treatment liquor is provided by adding 112 mL of the laundry detergent treatment composition described in Example 3 to 1.6 L of water. The resulting treatment liquor contains about 10400 ppm citric acid.

Example 5. Color Rejuvenation (1)

The following process is performed to demonstrate a color rejuvenation benefit and shows the use of a treatment composition according to the present disclosure. A first fabric and a second fabric are provided—two tank tops of identical color (100% cotton). Both fabrics are washed ten times with a powdered laundry detergent (ARM & HAMMER® plus Oxi Clean Stainfighters) and water characterized by a hardness of 18 gpg.

The second fabric is further treated with a treatment liquor that includes about 12000 ppm of citric acid (formed from the same treatment composition and dilution as described in Example 1 above). The second fabric is soaked in the treatment liquor for about twenty minutes. After soaking, the second fabric is provided to an automatic washing machine and run through a cycle with water only.

Figure 5:
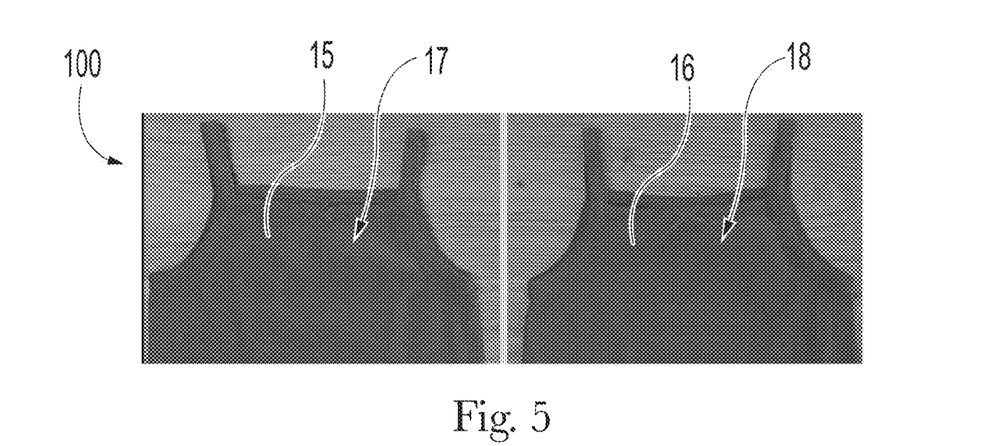
FIG. 5 shows a photographic display of a first fabric and a second fabric.

After drying, a first photograph of the first fabric is taken, and a second photograph of the second fabric is taken. FIG. 5 shows a display 100 of the photographs side-by-side. The first fabric 15 has a first color 17; the second fabric 16 has a second color 18. The second color 18 is a brighter color, and is closer to the original color of the fabric, than the first color 17 is.

The color differences between the first and second colors 17, 18 of the first and second fabrics 15, 16 are displayed in Table 1, as well as the "original" color of the fabric as new. Each L*a*b* reading is an average of three measurements, rounded to one decimal place.

TABLE 1

| Red Tank Tops | L* | a* | b* |
|---|---|---|---|
| Original Color (new) | 35.6 | 53.7 | 26.3 |
| Color 1/Fabric 1 (untreated) | 38.3 | 46.8 | 13.4 |
| Color 2/Fabric 2 (post-treatment) | 37.1 | 53.3 | 22.0 |
| Pre-to-Post Treatment Difference (Color 2 − Color 1) | −1.2 | 6.5 | 15.1 |

It is noticeable that the L* value decreased, meaning that the second color is closer to black (e.g., may be darker) than is the first color. Additionally, the a* value increased, indicating that the second color is more red than the first color.

Additionally, the "original" color of the garment (e.g., a new fabric, prior to any washing by the consumer), is measured, and color differences between the original color (as new), the first color (e.g., faded), and the second color (e.g., rejuvenated) are provided as ΔE values. The results are below in Table 2.

TABLE 2

| # | Comparison | ΔE |
|---|---|---|
| 1 | Difference from Original Color to First Color (e.g., loss upon fading) | 14.6 |
| 2 | Difference from First Color to Second Color (e.g., color improvement from faded) | 10.9 |
| 3 | Difference from Original Color to Second Color (e.g., difference between new fabric and rejuvenated fabric) | 4.6 |

As shown by the results in Table 2, the color changed significantly from the original color to the first color (new to faded). The color also changed significantly from the first to the second color (faded to post-treatment). Finally, comparing the first row to the third row, the difference between the original color and the second color (4.6) is smaller than the difference between the original color and the first color (14.6) indicating that the second color is closer to the original color than the first color is. In other words, much of the seemingly-lost color has been recovered following treatment according to the present disclosure.

Example 6. Color Rejuvenation (2)

The following process is performed to demonstrate a color rejuvenation benefit and shows the use of a treatment composition according to the present disclosure. A first fabric and a second fabric are provided—two infant outfits of identical design and color, including a dark blue fabric that includes small hearts of various colors (pink, light blue, yellow, white), as well as the phrase "LITTLE SISTER" in pink. Both fabrics (100% cotton—infant "onesies") are washed ten times with a powdered laundry detergent (ARM & HAMMER® plus Oxi Clean Stainfighters) and water characterized by a hardness of 18 gpg.

The second fabric is further treated with the treatment liquor and treatment process described in Example 5.

Figure 6:
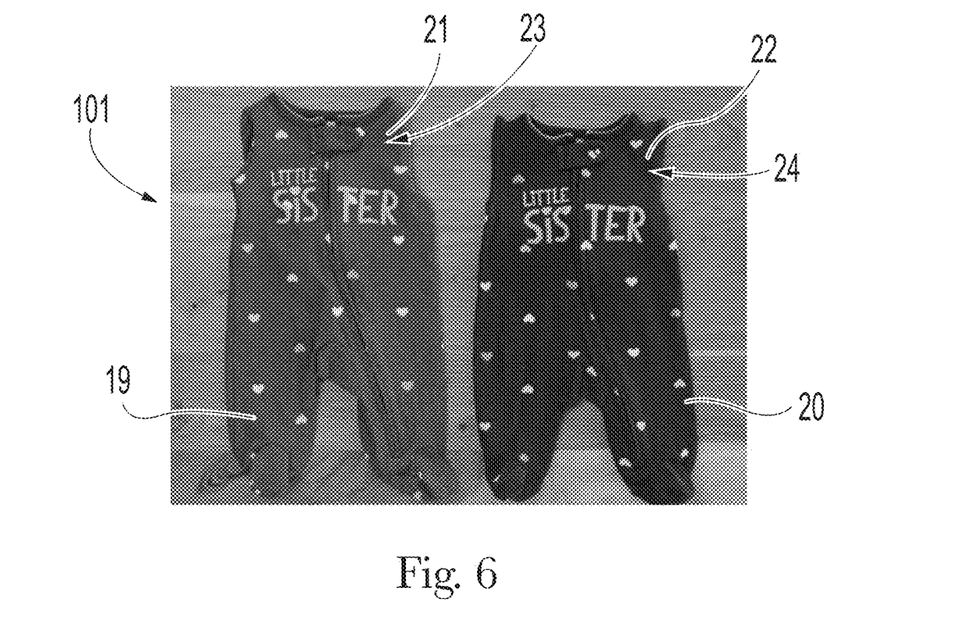
FIG. 6 shows a photographic display of a first fabric and a second fabric, where each includes a plurality of colors.
Figure 7:
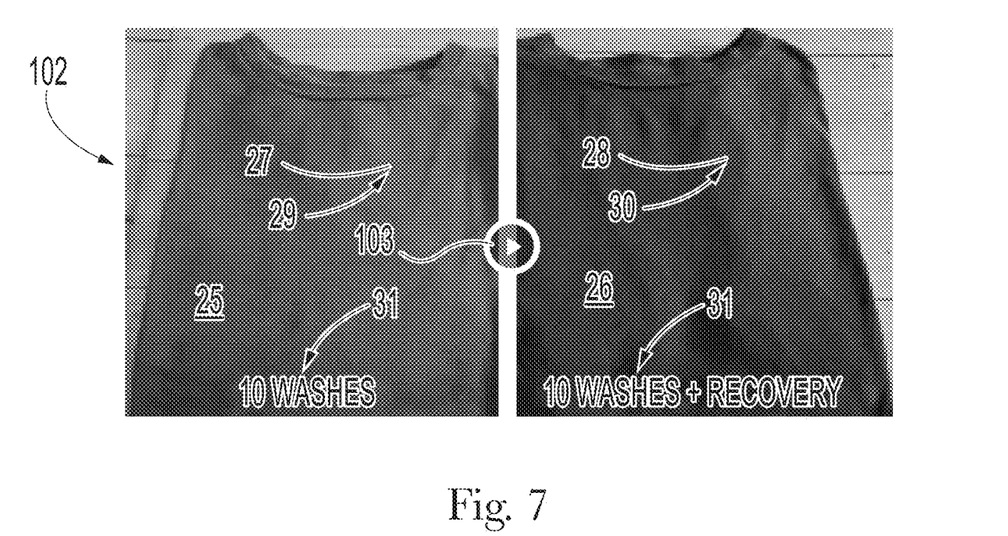
FIG. 7 shows a display in the form of a video still, showing a first fabric and a second fabric.

After drying, a photograph is taken of the first fabric and the second fabric side-by-side. FIG. 6 shows a display 101, namely the photograph. The first fabric 19 has a first color 23 (i.e., blue) at a first location 21; the second fabric 20 has a second color 24 (i.e., a darker/deeper blue) at a second location 22. The second color 24 is a darker color than the first color 23 is. The second color 24 is also closer to the original color of the fabric than the first color 23 is.

The color differences between the first and second colors 23, 24 of the first and second fabrics 19, 20 are displayed in Table 3. Each L*a*b* reading is an average of three measurements, rounded to one decimal place.

TABLE 3

| Blue Onesies | L* | a* | b* |
|---|---|---|---|
| Color 1/Fabric 1 (untreated) | 33.1 | 1.1 | −15.6 |
| Color 2/Fabric 2 (post-treatment) | 23.9 | 1.6 | −14.7 |
| Difference (Color 2 − Color 1) | −9.2 | 0.5 | 0.9 |

It is noticeable that the L* value decreased, meaning that the second color is closer to black (e.g., may be darker) than is the first color.

Additionally, the overall difference in color ($\Delta E$) between the second fabric and the first fabric is found to be 9.31, indicating that the second fabric has shown a color rejuvenation/color recovery benefit due to being treated with the treatment composition as described above.

Example 7. Color Rejuvenation (3)

The following process is performed to demonstrate a color rejuvenation benefit and shows the use of a treatment composition according to the present disclosure. A first fabric and a second fabric are provided—two identical black t-shirts (100% cotton). The first and second fabrics are treated as described in Example 5, including the additional treatment step of the second fabric with a treatment liquor formed by diluting a treatment composition in water.

After drying, a first photograph of the first fabric is taken, and a second photograph of the second fabric is taken. FIG. 6 shows a display 102, namely a still from a video (evidenced by a "play" button 103) featuring the two photographs side-by-side. The video still includes indicia 31 indicating which treatment each fabric was subjected to.

The first fabric 25 has a first color 29, for example at a first location 27; the second fabric 26 has a second color 30, for example at a second location 28. The second color 30 is a darker color than the first color 29 is. The second color 30 is also closer to the original color of the fabric than the first color 29 is.

The color differences between the first and second colors 29, 30 of the first and second fabrics 25, 26 are displayed in Table 4. Additionally, Whiteness Index measurements are provided (WI CIE), determined according to the test method provided above. Each reading is an average of three measurements, rounded to one decimal place.

TABLE 4

| Black T-shirts | L* | a* | b* | WI CIE |
|---|---|---|---|---|
| Color 1/Fabric 1 (untreated) | 16.1 | −0.3 | −1.7 | 29.3 |
| Color 2/Fabric 2 (post-treatment) | 12.7 | 0.4 | −0.6 | 11.2 |
| Difference (Color 2 − Color 1) | −3.4 | 0.7 | 1.1 | −18.1 |

As shown by the results in Table 3, the L* value of Color 2 is less than the L* value of Color 1, indicating that the fabric appears more black (e.g., is darker). Furthermore, the Whiteness Index has also decreased, meaning that Color 2 is less white than Color 1 (e.g., is darker). The overall difference in color ($\Delta E$) between the second fabric and the first fabric is relatively small ($\Delta E=3.7$), which may be expected as the shirts are black, which is typically thought of as the absence of color.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process to determine the presence of a metal-based residue on a fabric, the process comprising the steps of:
providing a vessel with a storage portion and an open mouth;
providing a treatment liquor to the storage portion of the vessel,
the treatment liquor comprising an organic acid,
optionally, forming the treatment liquor by combining a treatment composition and water, the treatment composition comprising the organic acid;
submerging at least a portion of the fabric in the treatment liquor for at least two seconds; and
detecting the presence of released metal-based residue into the treatment liquor, wherein the metal of the metal-based residue is calcium, magnesium, copper, aluminum, or mixtures thereof.

2. The process of claim 1, wherein the organic acid is selected from the group consisting of citric acid, acetic acid, lactic acid, malic acid, maleic acid, salts thereof, and mixtures thereof.

3. The process of claim 1, wherein the organic acid is citric acid, a salt thereof, or a mixture thereof.

4. The process of claim 1, wherein the organic acid is a naturally derived organic acid.

5. The process of claim 1, wherein the metal of the metal-based residue is calcium.

6. The process of claim 1, wherein the fabric was prewashed with a powdered laundry detergent.

7. The process of claim 6, wherein the prewashed fabric has been treated with a laundry detergent in at least two wash cycles.

8. The process of claim 1, wherein the fabric was prewashed in water having a hardness of from about 0 to about 30 grains per gallon (gpg).

9. The process of claim 1, wherein the treatment composition comprises from about 5% to about 50%, by weight of the treatment composition, of the organic acid, with the proviso that if the organic acid is acetic acid in the presence of no other organic acid, then the treatment composition comprises from 10% to about 50%, by weight of the treatment composition, of the acetic acid.

10. The process of claim 1, wherein the fabric comprises cotton fibers, polycotton fibers, or combinations thereof.

11. The process of claim 1, wherein the fabric comprises a plurality of colors.

12. The process of claim 1, wherein the metal-based residue is derived from an anionic surfactant, an anionic polymer, a carbonate, a silicate, or a combination thereof.

13. The process of claim 1, wherein the metal-based residue is derived from a laundry detergent.

14. The process of to claim 1, wherein the fabric is characterized by:
an original color when new;
a first color when faded; and
a second color following treatment with the treatment liquor;
where the difference in color ($\Delta E$) between of the original color and the second color is less than the difference in color ($\Delta E$) between the original color and the first color.

15. A process to determine the presence of a metal-based residue on a fabric, the process comprising the steps of:
providing a vessel with a storage portion and an open mouth;
providing a treatment liquor to the storage portion of the vessel, the treatment liquor comprising an organic acid, optionally, forming the treatment liquor by combining a treatment composition and water, the treatment composition comprising the organic acid;
submerging at least a portion of the fabric in the treatment liquor for at least two seconds; and
detecting the presence of released metal-based residue into the treatment liquor, wherein the metal-based residue is derived from an anionic surfactant, an anionic polymer, a carbonate, a silicate, or a combination thereof.

16. The process of claim 15, wherein the metal-based residue is derived from a laundry detergent.

17. The process of to claim 15, wherein the fabric is characterized by:
an original color when new;
a first color when faded; and
a second color following treatment with the treatment liquor;
where the difference in color ($\Delta E$) between of the original color and the second color is less than the difference in color ($\Delta E$) between the original color and the first color.

* * * * *